United States Patent [19]
Peterson

[11] Patent Number: 5,985,592
[45] Date of Patent: Nov. 16, 1999

[54] USES FOR PENTOXIFYLLINE OR FUNCTIONAL DERIVATIVES/METABOLITES THEREOF

[75] Inventor: Theresa C. Peterson, Nova Scotia, Canada

[73] Assignee: Dalhousie University, Halifax, Canada

[21] Appl. No.: 08/870,096

[22] Filed: Jun. 5, 1997

[51] Int. Cl.[6] .............................. C12Q 1/02; C12Q 1/00; C12Q 1/50; G01N 33/53

[52] U.S. Cl. .................................. 435/29; 435/4; 435/17; 435/975; 424/9.1; 424/277.1; 424/93.1; 424/553; 424/551

[58] Field of Search .................................. 435/29, 4, 17, 435/975; 424/9.1, 277.1, 93.1, 553, 551

[56] References Cited

U.S. PATENT DOCUMENTS

| | | | |
|---|---|---|---|
| 4,160,452 | 7/1979 | Theeuwes | 128/260 |
| 4,256,108 | 3/1981 | Theeuwes | 128/260 |
| 4,265,874 | 5/1981 | Bonsen et al. | 424/15 |
| 5,077,296 | 12/1991 | Drizen | 514/261 |
| 5,096,906 | 3/1992 | Mandell et al. | 514/261 |
| 5,366,978 | 11/1994 | Furukawa et al. | 514/263 |

OTHER PUBLICATIONS

Bamberger et al., "Modulation of AP–1 activity by the human progesterone receptor in endometrial adenocarcinoma cells" *Proc. Natl. Acad. Sci. USA*, 93:6169–6174 (1996).

Bessler et al., "Effect of Pentoxifylline on the Phagocytic Activity, cAMP Levels, and Superoxide Anion Production by Monocytes and Polymorphonuclear Cells" *J. Leukocyte Biol.*, 40:747–754 (1986).

Bogoyevitch, et al., "Cellular Stresses Differentially Activate c–Jun N–terminal Protein Kinases and Extracellular Signal–regulated Protein Kinases in Cultured Ventricular Myocytes" *J. Biol. Chem.*, 270(50):29710–17 (1995).

Buchdunger et al., "Inhibition of the Abl Protein–Tyrosine Kinase in Vitro and in Vivo by a 2–Phenylaminopyrimidine Derivative" *Cancer Res.*, 56:100–4 (1996).

(List continued on next page.)

*Primary Examiner*—Louise N. Leary
*Attorney, Agent, or Firm*—Stephen E. Reiter; Gray Cary Ware & Freidenrich, LLP; Stanley H. Kim

[57] ABSTRACT

In accordance with the present invention, it has been discovered that monocyte conditioned medium (MCM) obtained from patients with liver disease stimulates the proliferation of fibroblasts. Platelet derived growth factor (PDGF) has also been found to stimulate fibroproliferation of fibroblasts, and to be at least partially responsible for the fibroproliferative effect of the MCM. Further in accordance with the present invention, the effect of MCM and PDGF on the expression of c-fos and c-jun has been investigated, because c-fos and c-jun form AP-1 complexes which can stimulate genes involved in proliferation. It has recently been reported that pentoxifylline inhibits platelet derived growth factor-stimulated proliferation. The mechanism of this action of pentoxifylline is unclear. Thus, in the course of the work undertaken as part of the present invention, studies were conducted to determine whether pentoxifylline altered the expression of c-fos and c-jun. While PDGF was found to induce the expression of both c-fos and c-jun, pentoxifylline was found to effectively reduce the effect of PDGF-induced c-jun gene expression, without altering c-fos gene expression. These results suggest that pentoxifylline inhibits PDGF stimulated proliferation by decreasing c-jun expression. These results further suggest a variety of diseases and/or conditions which may also be successfully treated with pentoxifylline.

20 Claims, 8 Drawing Sheets

OTHER PUBLICATIONS

Burgering et al., "cAMP antagonizes p21$^{ras}$–directed activation of extracellular signal–regulated kinase 2 and phosphorylation of mSos nucleotide exchange factor" *The EMBO Journal*, 12(11):4211–4220 (1993).

Cimminiello et al., "Platelet–Derived Growth Factor (PDGF) in Patients with Different Degrees of Chronic Arterial Obstructive Disease" *Angiology*, 45(4):289–293 (1994).

Coso et al., "Transforming G Protein–coupled Receptors Potently Activate JNK (SAPK)" *J. Biol. Chem.*, 270(10):5620–5624 (1995).

Crespo et al., "Signaling through Transforming G Protein–coupled Receptors in NIH 3T3 Cells Involves c–Raf Activation" *J. Biol. Chem.*, 269(33):21103–21109 (1994).

Davis, "The Mitogen–activated Protein Kinase Signal Transduction Pathway" R.J. *J. Biol. Chem.*, 268(20):14553–14556 (1993).

Dohlman et al. "Generation of a unique fibroblast–activating factor by human monocytes" *Immunol.*, 52:577–584 (1984).

Gesualdo et al., "Platelet–Derived Growth Factor Expression in Mesangial Proliferative Glomerulonephritis" *Lab Invest.*, 65(2):160–167 (1991).

Herschman, H. R., "Primary Response Genes Induced by Growth Factors and Tumor Promoters" *Ann. Rev. of Biochem.*, 60:281–319 (1991).

Hunter and Karin, "the Regulation of Transcription by Phosphorylation" *Cell*, 70:375–387 (1992).

Lo et al., "Reactive Oxygen Species Mediate Cytokine Activation of c–Jun NH$_2$–terminal Kinases*" *J. Biol. Chem.*, 271(26):15703–15707 (1996).

Leon and Rojkind, "A Simple Micromethod for Collagen and Total Protein Determination in Formalin–fixed Paraffin–embedded Sections[1,2]" *J. Histochem. and Cytochem.*, 33(8):737–743 (1985).

Luke and Rocci, "Determination of pentoxifylline and a major metabolite, 3,7–demethyl–1–(5'–hydroxyhexy)xanthine, by high–performance liquid chromatography" *J. Chromatogr.*, 374(1):191–195 (1986).

Marra et al., "Involvement of phosphatidylinositol 3–kinase in the activation of extracellular signal–regulated kinase by PDGF in hepatic stellate cells" *FEBS Lett.*, 376:141–145 (1995).

McCormick, F., "How receptors turn Ras on" *Nature*, 363:15–16 (1993).

Meskini et al., "Phosphodiesterase Inhibitory Profile of Some Related Xanthine Derivatives Pharmacologically Active on the Peripheral Microcirculation" *Biochem. Pharmacol.*, 47(5):781–788 (1994).

Nakamura et al., "Renal Platelet–Derived Growth Factor Gene Expression in NZB/W F1 Mice with Lupus and ddY Mice with IgA Nephropathy" *Clin. Immunol. Immunopathol.*, 63(2):173–181 (1992).

Palech, S.L., "Networking with protein kinases" *Curr. Biol.*, 3(8):513–515 (1993).

Pesonen, E., "Infection and intimal thickening: evidence from coronary arteries in children" *Eur. Heart J.*, 15(Suppl X):57–61 (1994).

Peterson, "Interleukin–1, platelet derived growth factor, free radicals and monocyte aryl hydrocarbon hydroxylase activity in liver disease. Role of cell communication" *Biochem. Pharmacol.*, 43(5):1163–1166 (1992).

Peterson, T. C., "Pentoxifylline Prevents Fibrosis in an Animal Model and Inhibits Platelet–derived Growth Factor–driven Proliferation of Fibroblasts" *Hepatol.*, 17(3):486–493 (1993).

Peterson, T.C. "Inhibition of Fibroproliferation by Pentoxifylline Activity of Metabolite–1 and Lack of Role of Adenosine Receptors" *Biochem. Pharmacol.*, 52:597–602 (1996).

Peterson and Isbrucker, "Fibroproliferation in Liver Disease: Role of Monocyte Factors" *Hepatol.*, 15(2):191–197 (1992).

Peterson and Neumeister, "Effect of pentoxifylline in rat and swine models of hepatic fibrosis: role of fibroproliferation in its mechanism" *Immunopharmacol.*, 31:183–193 (1996).

Peterson and Tanton, "Effect of Pentoxifylline In Collagenous Colitis" *Can. J. Gastroenterol.*, 10:S76 (1996).

Peterson et al., "In vitro effect of platelet–derived growth factor on fibroproliferation and effect of cytokine antagonists" *Immunopharmacol.*, 28:259–270 (1994).

Pietrogrande et al., "A Role for Platelet–Derived Growth Factor in Drug–Induced Chronic Ergotism? A Case Report" *Angiology*, 46(7):633–636 (1995).

Rosenwald et al., "Transient inhibition of protein synthesis induces expression of proto–oncogenes and stimulates resting cells to enter the cell cycle" *Cell Prolif.* 28:631–644 (1995).

Schafer et al., "PACAP Stimulates Transcription of c–Fos and c–Jun and Activates the P–1 Transcription Factor in Rat Pancreatic Carcinoma Cells" *Biochem. Biophys. Res. Commun.*, 221:111–116 (1996).

Schlesinger, J., "How receptor tyrosine kinases activate Ras" *Trends Biochem. Sci.*, 18:273–275 (1993).

Shaw et al., "Pathogenesis of Pulmonary Fibrosis in Interstitial Lung Disease" *Am. Rev. Respir. Dis.*, 143:167–173 (1991).

Terano et al., "Eicosapentaenoic Acid Suppressed the Proliferation of Vascular Smooth Muscle Cells Through Modulation of Various Steps of Growth Signals" *Lipids*, 31:S301–S304 (1996).

Uebelhoer et al., "Modulation of Fibroblast Activity in Histiocytosis X by Platelet–Derived Growth Factor" *Chest.*, 107:701–705 (1995).

Wu et al., "Inhibition of the EGF–Activated MAP Kinase Signaling Pathway by Adenosine 3',5'–Monophosphate" *Science*, 262:1065–1069 (1993).

Xie and Hershcan, "v–src Induces Prostaglandin Synthase 2 Gene Expression by Activation of the c–June N–terminal Kinase and the c–June Transcription Factor*" *J. Biol. Chem.*, 270:27622–27628 (1995).

Zar, J.H. in Biostatistical methods. Prentice–Hall (Englewood Cliffs, N.J., 1974).

USES FOR PENTOXIFYLLINE OR FUNCTIONAL DERIVATIVES/ METABOLITES THEREOF

FIELD OF THE INVENTION

The present invention relates to novel uses for pentoxifylline or functional derivatives/metabolites thereof. In a particular aspect, the present invention relates to methods for the treatment of diseases and/or conditions characterized by elevated levels of such factors as platelet derived growth factor (PDGF), inflammatory cytokine(s), and the like.

BACKGROUND OF THE INVENTION

Collagenous colitis was first described by Lindstrom as chronic watery diarrhea (Pathol. Eur. 11(1):87–89 (1976)). Collagenous colitis is characterized by collagen deposition, likely resulting from an imbalance between collagen production by mucosal fibroblasts and collagen degradation. Very little is understood, however, regarding the mechanism by which collagenous colitis results in secretory diarrhea.

The incidence of collagenous colitis is similar to primary biliary cirrhosis. This disease has an annual incidence of 1.8 per 100,000 and a prevalence of 15.7 per 100,000, which is similar to primary biliary cirrhosis (12.8 per 100,000) and lower than ulcerative colitis (234 per 100,000), Crohn's disease (146 per 100,000) or celiac disease (5 per 100,000). In patients with chronic diarrhea, about 0.3 to 5% have collagenous colitis.

In efforts to characterize the patients under study, sera and monocyte conditioned media (MCM) from patients with collagenous colitis have been assessed for their ability to stimulate fibroproliferation. Cytokine antibodies were used to characterize the fibroproliferative component of patient samples.

Previous studies have suggested that MCM samples obtained from patients with liver disease are capable of stimulating proliferation of fibroblasts (see Peterson and Isbrucker, in Hepatol. 15(2):191–197 (1992)). It has also been established that several genes involved in proliferation possess AP-1 binding sites, and thus would be expected to be susceptible to regulation by the immediate early genes c-fos and c-jun (see, for example, Schafer et al., in Biochem. Biophys. Res. Commun. 221:111–116 (1996) and Bamberger et al., in Proc. Natl. Acad. Sci. USA 93:6169–6174 (1996)).

In order to determine whether these immediate early genes are upregulated by MCM obtained from patients with liver disease, the effect of MCM from patients with liver disease was investigated. MCM exerts many effects due to PDGF (see, for example, Peterson and Isbrucker in Hepatol. 15(2):191–197 (1992) and Peterson and Tanton in Can. J. Gastroenterol. 10:S76 (1996)). Indeed, it has been established that PDGF itself stimulates proliferation of fibroblasts (see Peterson, T. C. in Hepatol. 17(3):486–493 (1993) and Peterson et al., in Immunopharmacol. 28:259–270 (1994). Thus, the question of whether PDGF upregulates the expression of c-fos and c-jun was addressed.

Prior studies have indicated that pentoxifylline inhibits PDGF and MCM stimulated proliferation (see, for example, Peterson, T. C. in Hepatol. 17(3):486–493 (1993), Peterson et al., in Immunopharmacol. 28:259–270 (1994) and Peterson and Neumeister in Immunopharmacol. 31:183–193 (1996)). The mechanism for this effect of pentoxifylline remains unclear, but does not appear to involve competing for the PDGF receptor or adenosine receptor activation (see Peterson, T. C. in Biochem. Pharmacol. 52:597–602 (1996)). One possible mechanism for the inhibitory effect of pentoxifylline on PDGF-stimulated proliferation is inhibition of PDGF post-receptor signalling. Thus, in accordance with the present invention, it was undertaken to determine if pentoxifylline modified the effect of PDGF on immediate early gene expression.

Accordingly, there is a need in the art to achieve a better understanding of the mechanism by which agents such as pentoxifylline are effective for the treatment of collagenous colitis. Based upon a more complete understanding of the mechanism by which such agents are effective for the treatment of collagenous colitis, it may be possible to apply this understanding to the development of new methods of treatment for a variety of idications which are in no way related to collagenous colitis.

BRIEF DESCRIPTION OF THE INVENTION

In accordance with the present invention, it has been discovered that monocyte conditioned medium (MCM) obtained from patients with liver disease stimulates the proliferation of fibroblasts. Platelet derived growth factor (PDGF) has also been found to stimulate fibroproliferation of fibroblasts, and to be at least partially responsible for the fibroproliferative effect of the MCM.

Further in accordance with the present invention, the effect of MCM and PDGF on the expression of c-fos and c-jun has been investigated, because c-fos and c-jun form AP-1 complexes which can stimulate genes involved in proliferation.

It has recently been reported that pentoxifylline inhibits platelet derived growth factor-stimulated proliferation. The mechanism of this action of pentoxifylline is unclear. Thus, in the course of the work undertaken as part of the present invention, studies were conducted to determine whether pentoxifylline altered the expression of c-fos and c-jun. While PDGF was found to induce the expression of both c-fos and c-jun, pentoxifylline was found to effectively reduce the effect of PDGF-induced c-jun gene expression, without altering c-fos gene expression. These results suggest that pentoxifylline inhibits PDGF stimulated proliferation by decreasing c-jun expression. These results further suggest a variety of diseases and/or conditions which may also be successfully treated with pentoxifylline.

Figure 1A:
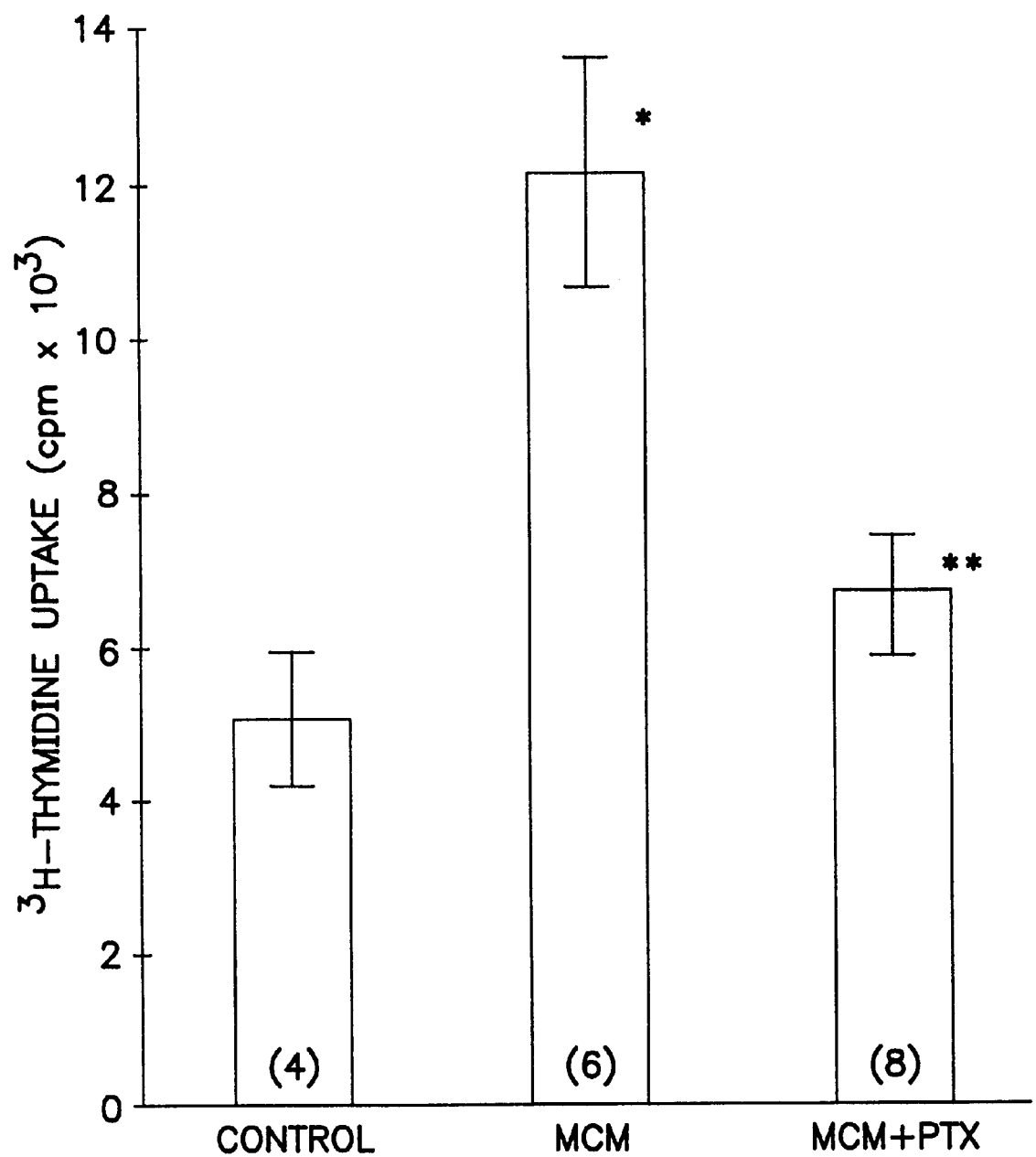
FIG. 1A illustrates the effect of MCM obtained from patients with liver disease on fibroproliferation when incubated either with 240 μM pentoxifylline, or without added pentoxifylline.
Figure 1B:
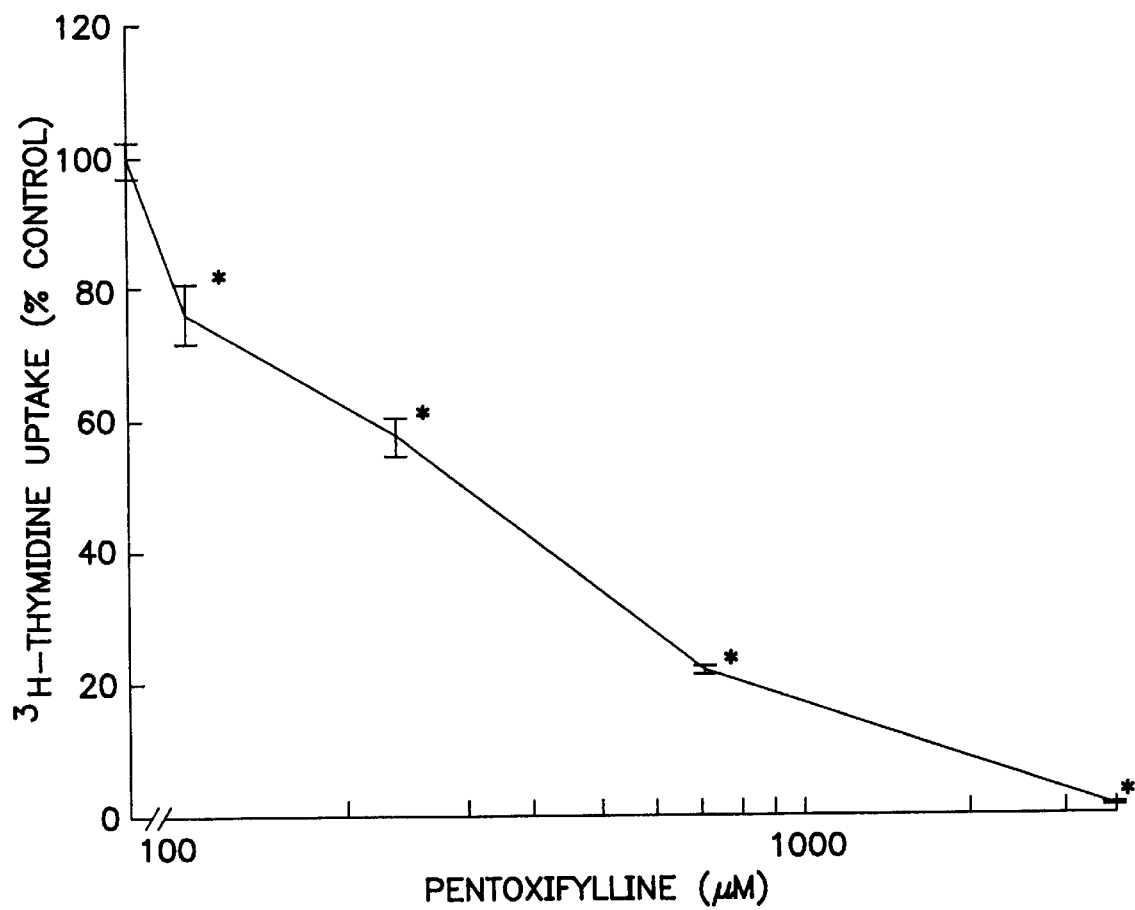
FIG. 1B illustrates the effect of MCM obtained from patients with liver disease on fibroproliferation when incubated with increasing amounts of pentoxifylline.
Figure 1C:
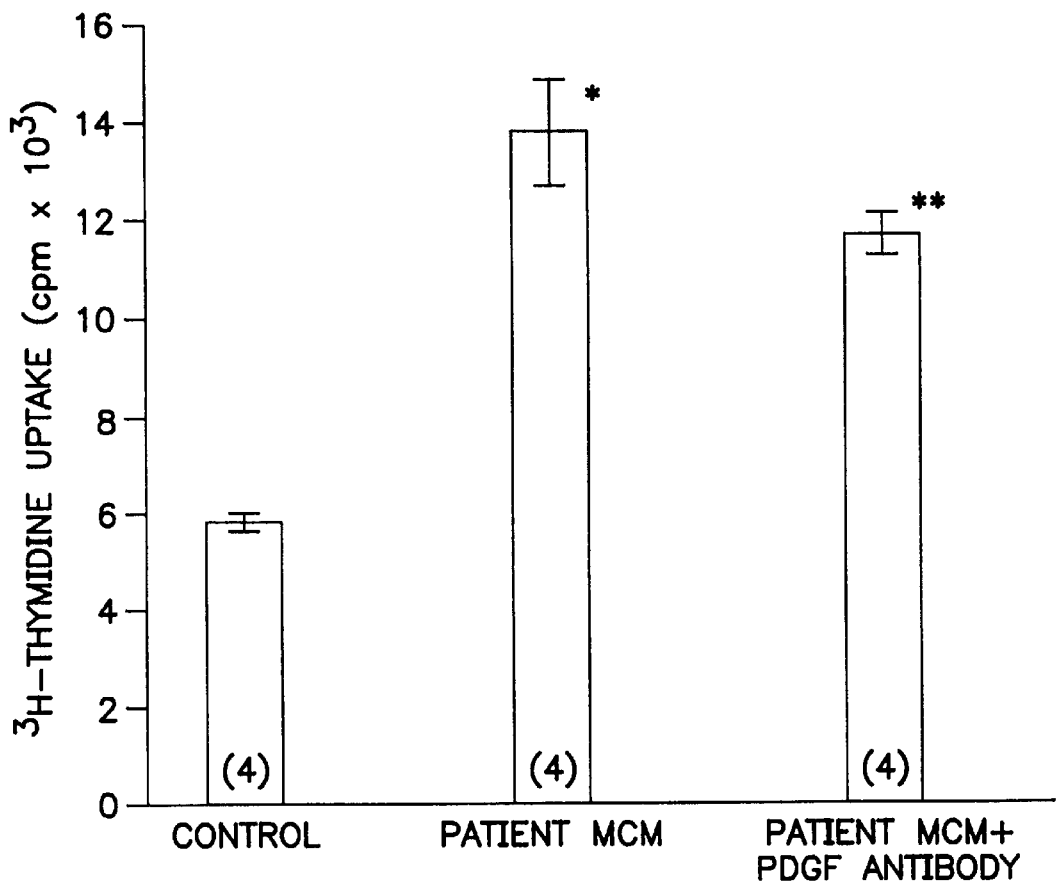
FIG. 1C illustrates the effect of MCM obtained from patients with liver disease on fibroproliferation, with and without preincubation with PDGF antibody.

For each of FIGS. 1A, 1B and 1C, fibroproliferaton was assessed as tritiated thymidine uptake by fibroblasts in counts per minute (cpm). MCM was prepared from blood obtained from liver disease patients (n=6) as described in Example 1. Pentoxifylline (PTX) was assessed over a range of concentrations, as indicated in FIG. 1B. PDGF antibody (50 μg/ml) was preincubated with MCM for 1 hr prior to testing on fibroblasts. Results are expressed as mean ±S.E. Each treatment was done on wells in quadruplicate and experiments were repeated. *(p<0.05) compared to fibroblasts incubated with control medium. (p<0.05) compared to fibroblasts stimulated with MCM in the absense of pentoxifylline. *(p<0.05) compared to fibroblasts stimulated with MCM in the absence of PDGF antibody.

Figure 2:
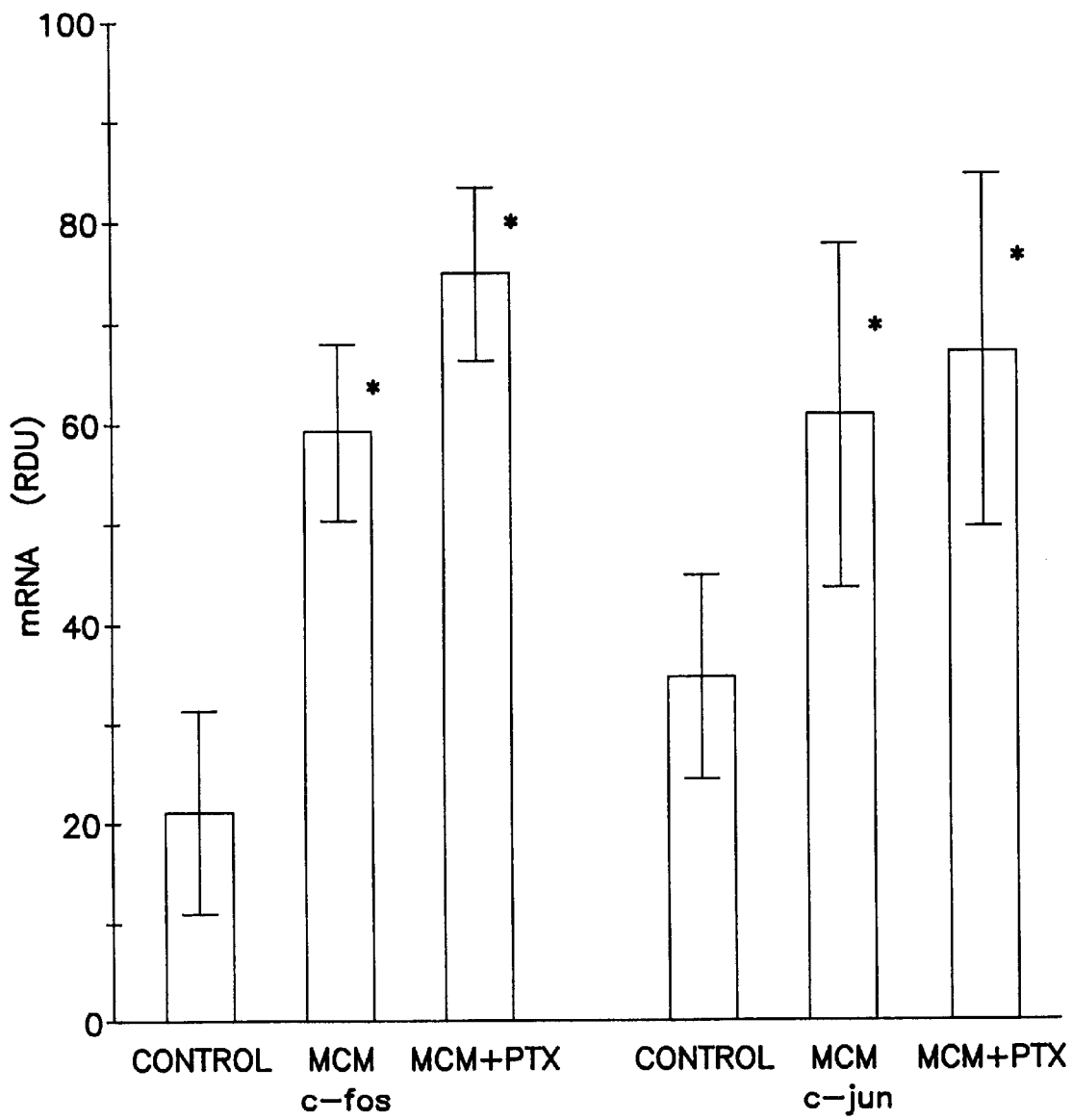

FIG. 2 presents the results of phosphorimaging analysis illustrating the effect of MCM obtained from patients with liver disease, with and without incubation with pentoxifylline (3.5 mM, for 30 min), on the expression of c-fos and c-jun. The figure combines the results obtained from three independent experiments. *=p<0.05 compared to control.

Figure 3:
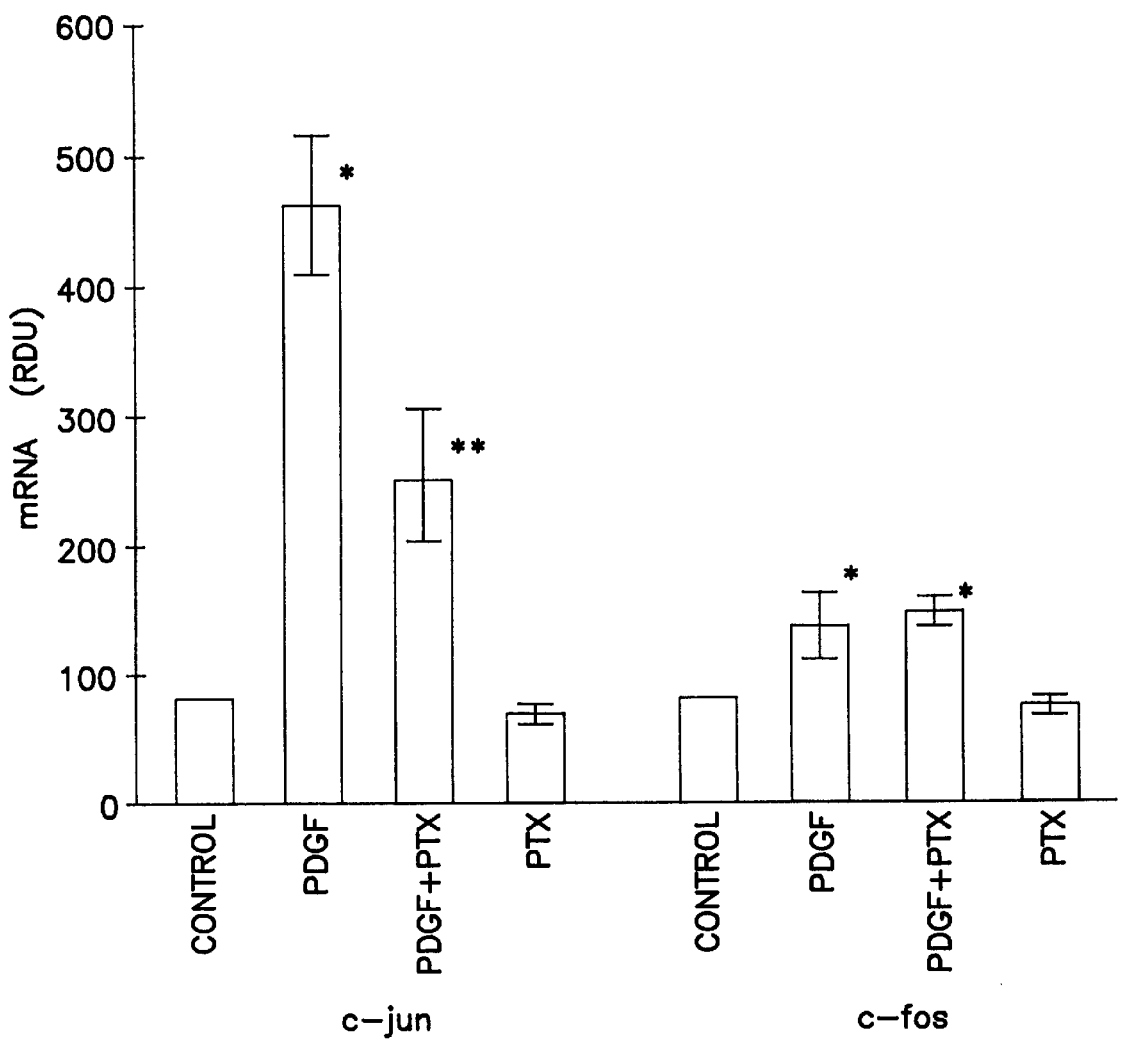

FIG. 3 presents the results of phosphorimaging analysis illustrating the effect of PDGF, with and without pentoxifylline, on the expression of c-fos and c-jun. The figure combines the results of three indepenent experiments. *=significantly different (p<0.05) compared to control or PTX alone. +=significantly different (p<0.05) compared to PDGF.

Figure 4:
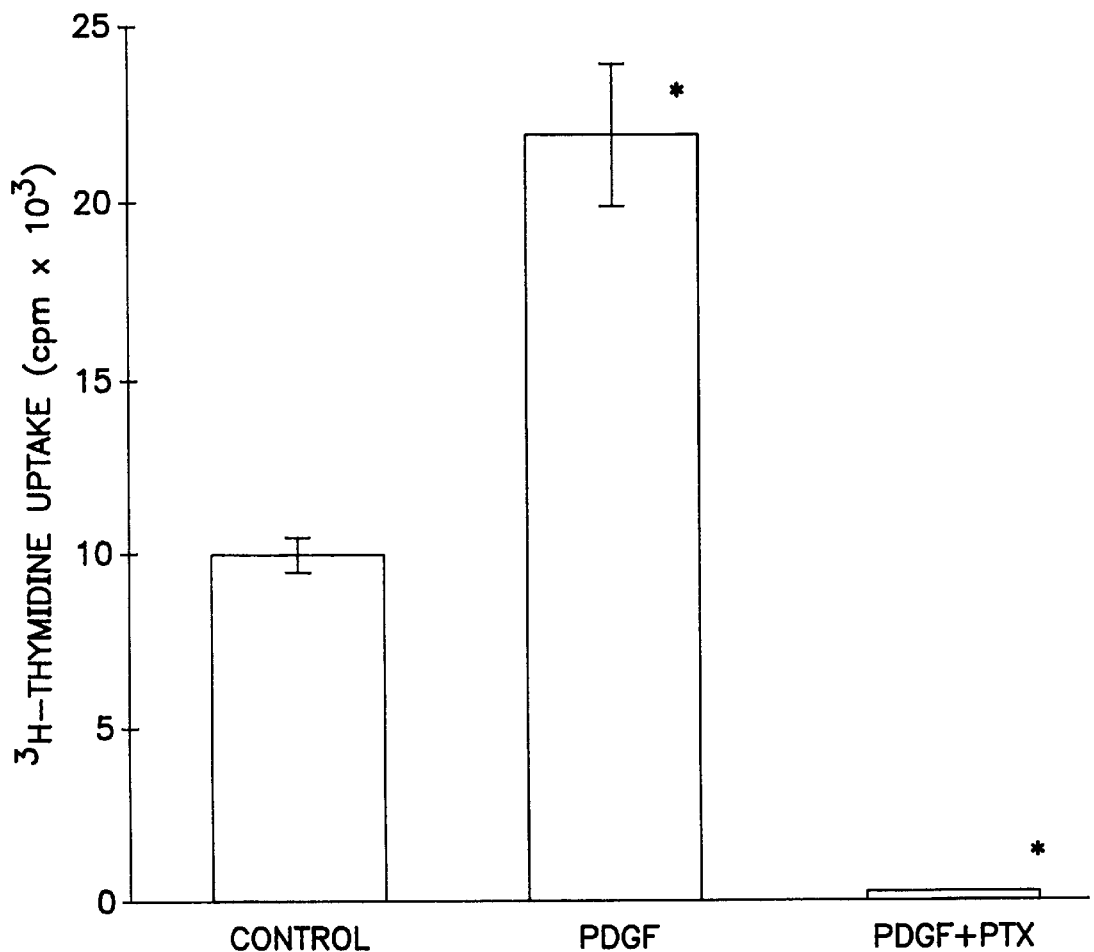
Figure 5:
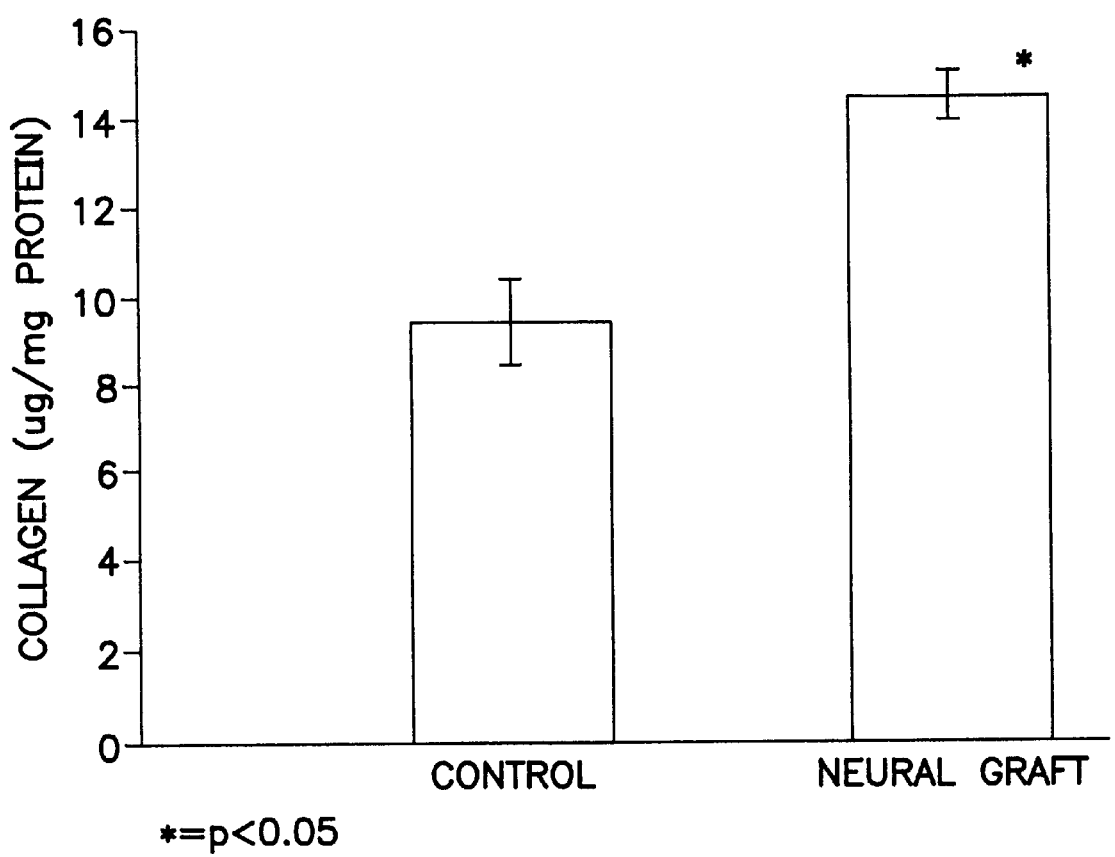
Figure 6:
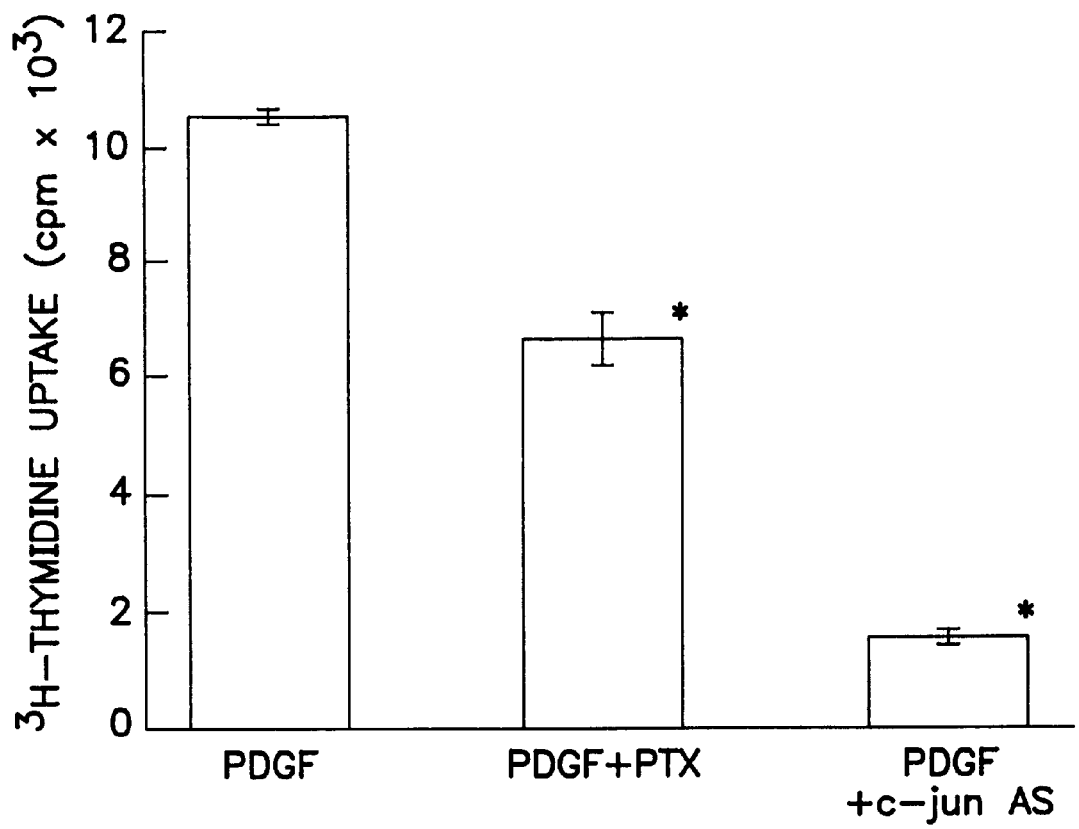

FIG. 4 illustrates the effect of pentoxifylline on PDGF stimulated proliferation. Fibroproliferation was assessed as tritiated thymidine uptake by fibroblasts in counts per minute (cpm). Pentoxifylline (PTX) was assessed at 3.5 mM (1 mg/ml), PDGF was tested at 8 ng/ml. Results were expressed as mean ±S.E. Each treatment was done on wells in quadruplicate and experiments were repeated. *(p<0.05) compared to fibroblasts without PDGF. +(p<0.05) compared to fibroblasts stimulated with PDGF in the absence of pentoxifylline.

DETAILED DESCRIPTION OF THE INVENTION

In accordance with the present invention, there are provided methods for the treatment of a subject afflicted with a disease and/or condition characterized by one or more of the following:

elevated platelet derived growth factor (PDGF) levels (e.g., elevated levels of PDGF-AA, PDGF-BB, PDGF-AB), elevation of Jun kinase, elevation of c-jun, activation of NF-kappaB or NF-kappaB p65, neutrophil infiltration, or elevated levels of inflammatory cytokine(s) (e.g., elevated levels of tumor necrosis factor (TNF), interleukin-1 (IL-1), interleukin-4 (IL-4), interleukin-12 (IL-12), insulin growth factor-1 (IGF-1), insulin growth factor-2 (IGF-2), TGF-alpha, TGF-beta, epidermal growth factor (EGF), nerve growth factor (NGF), acidic fibroblast growth factor (aFGF), basic fibroblast growth factor (bFGF), and the like), provided, however, that said disease or condition is not collagenous colitis, said method comprising administering to said subject an amount of pentoxifylline or functional derivatives/metabolites thereof effective to ameliorate the symptoms of said disease and/or condition.

As employed herein, reference to "elevated platelet derived growth factor (PDGF) levels" embraces species such as PDGF-AA, PDGF-BB, PDGF-AB, and the like, which are present at levels which are significantly higher than levels which are considered to be normal.

As employed herein, the phrase "elevated levels of inflammatory cytokine(s)" embraces such cytokines as tumor necrosis factor (TNF), interleukin-1(IL-1), interleukin-4 (IL-4), interleukin-12 (IL-12), insulin growth factor-1 (IGF-1), insulin growth factor-2 (IGF-2), TGF-alpha, TGF-beta, epidermal growth factor (EGF), nerve growth factor (NGF), acidic fibroblast growth factor (aFGF), basic fibroblast growth factor (bFGF), and the like, wherein said cytokines are present at levels which are significantly higher than levels which are considered to be normal.

As readily recognized by those of skill in the art, a wide variety of diseases and/or conditions are characterized as described herein, i.e., by one or more of the following:

elevated PDGF levels, elevation of Jun kinase, elevation of c-jun, activation of NF-kappaB or NF-kappaB p65, neutrophil infiltration, or elevated levels of inflammatory cytokine(s).

Examples of disease states and/or conditions which are contemplated for treatment according to the invention include interstitial lung disease, human fibrotic lung disease (e.g., idiopathic pulmonary fibrosis (IPF), adult respiratory distress syndrome (ARDS), tumor stroma in lung disease, systemic sclerosis, Hermansky-Pudlak syndrome (HPS), coal worker's pneumoconiosis (CWP), chronic pulmonary hypertension, AIDS associated pulmonary hypertension, and the like), human kidney disease (e.g., nephrotic syndrome, Alport's syndrome, HIV-associated nephropathy, polycystic kidney disease, Fabry's disease, diabetic nephropathy, and the like), glomerular nephritis, nephritis associated with systemic lupus, liver fibrosis, myocardial fibrosis, pulmonary fibrosis, Grave's ophthalmopathy, drug induced ergotism, cardiovascular disease, cancer, Alzheimer's disease, scarring, scleroderma, glioblastoma in Li-Fraumeni syndrome, sporadic glioblastoma, myeloid leukemia, acute myelogenous leukemia, myelodysplastic syndrome, myeloproliferative syndrome, gynecological cancer (e.g., ovarian cancer, Lynch syndrome, and the like), Kaposi's sarcoma, Hansen's disease, inflammatory bowel disease (including stricture formation in Crohn's disease), but not including collagenous colitis, and the like.

As used herein, the phrase "pentoxifylline or functional derivatives/metabolites thereof" refers to the compound 1-(5-oxohexyl)-3,7-dimethylxanthine (pentoxifylline), and oxidation-, reduction-, substitution- and/or rearrangement-products thereof, such as, for example, metabolite-1 through metabolite-7 as described by Luke and Rocci in J. Chromatogr. 374(1):191–195 (1986) (e.g., 1-(5-hydroxyhexyl)-3,7-dimethyl-xanthine (metabolite-1)), as well as synthetic variants thereof (e.g., propentofylline).

The active components described for use herein can be delivered in a suitable vehicle, thereby rendering such compositions amenable to oral delivery, transdermal delivery, subcutaneous delivery (e.g., intravenous delivery, intramuscular delivery, intraarterial delivery, intraperitoneal delivery, and the like), topical delivery, inhalation delivery, osmotic pump, and the like.

Depending on the mode of delivery employed, the above-described compositions can be delivered in a variety of pharmaceutically acceptable forms. For example, the above-described compositions can be delivered in the form of a solid, solution, emulsion, dispersion, micelle, liposome, and the like.

Pharmaceutical compositions contemplated for use in the practice of the present invention can be used in the form of a solid, a solution, an emulsion, a dispersion, a micelle, a liposome, and the like, wherein the resulting composition contains one or more of the active compounds contemplated for use herein, as active ingredients thereof, in admixture with an organic or inorganic carrier or excipient suitable for enteral or parenteral applications. The active ingredients may be compounded, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. The active compounds contemplated for use herein are included in the pharmaceutical composition in an amount sufficient to produce the desired effect upon the target process, condition or disease.

Pharmaceutical compositions containing the active ingredients contemplated herein may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known in the art for the manufacture of pharmaceutical compositions. In addition, such compositions may contain one or more agents selected from a sweetening agent (such as sucrose, lactose, or saccharin), flavoring agents (such as peppermint, oil of wintergreen or cherry), coloring agents and preserving agents, and the like, in order to provide pharmaceutically elegant and palatable preparations. Tablets containing the active ingredients in admixture with non-toxic pharmaceutically acceptable excipients may also be manufactured by known methods. The excipients used may be, for example, (1) inert diluents such as calcium carbonate, lactose, calcium phosphate, sodium phosphate, and the like; (2) granulating and disintegrating agents such as corn starch, potato starch, alginic acid, and the like; (3) binding agents such as gum tragacanth, corn starch, gelatin, acacia, and the like; and (4) lubricating agents such as magnesium stearate, stearic acid, talc, and the like. The tablets may be uncoated or they may be coated by known techniques to delay disintegration and absorption in the gastrointestinal tract, thereby providing sustained action over a longer period. For example, a time delay material such as glyceryl monostearate or glyceryl distearate may be employed. They may also be coated by the techniques described in the U.S. Pat. Nos. 4,256,108; 4,160,452; and 4,265,874, to form osmotic therapeutic tablets for controlled release.

In some cases, formulations for oral use may be in the form of hard gelatin capsules wherein the active ingredients are mixed with an inert solid diluent, for example, calcium carbonate, calcium phosphate, kaolin, or the like. They may also be in the form of soft gelatin capsules wherein the active ingredients are mixed with water or an oil medium, for example, peanut oil, liquid paraffin, or olive oil.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

Compositions contemplated for use in the practice of the present invention may also be administered in the form of suppositories for rectal administration of the active ingredients. These compositions may be prepared by mixing the active ingredients with a suitable non-irritating excipient, such as cocoa butter, synthetic glyceride esters of polyethylene glycols (which are solid at ordinary temperatures, but liquify and/or dissolve in the rectal cavity to release the active ingredients), and the like.

In addition, sustained release systems, including semipermeable polymer matrices in the form of shaped articles (e.g., films or microcapsules) can also be used for the administration of the active compound employed herein. Sustained release pentoxifylline compositions also include liposomally entrapped pentoxifylline.

Since individual subjects may present a wide variation in severity of symptoms and each active ingredient has its unique therapeutic characteristics, it is up to the practitioner to determine a subject's response to treatment and vary the dosages accordingly. Effective pentoxifylline levels for a given patient can readily be achieved by monitoring the patient using commonly available techniques, such as, for example, by subjecting serum obtained from the patient to high performance liquid chromatography (HPLC). The practitioner can then determine whether increased or decreased dosages of pentoxifylline are indicated, based on the level detected in the patient's serum.

Typical daily doses of the active component, in general, lie within the range of from about 10 $\mu$g up to about 100 mg per kg body weight, and, preferably within the range of from about 50 $\mu$g up to about 50 mg per kg body weight and can be administered up to four times daily. The daily dose lies within the range of from about 1 $\mu$g to about 100 mg per kg body weight, and, preferably, within the range of from 10 $\mu$g to 10 mg per kg body weight. Where one will operate within the above ranges will vary based on a variety of considerations, such as, for example, the age of the patient, the size of the patient, what, if any, other medications the patient may be taking (especially steroids), and the like.

As readily recognized by those of skill in the art, the active compounds contemplated for use herein can be administered as part of a slow release formulation, as a single bolus for rapid administration, as part of a depot formulation, as part of a nutritional supplement, and the like.

In another aspect of the present invention, a combination treating agent can be employed for the treatment of diseases and/or conditions characterized by elevated levels of such factors as platelet derived growth factor (PDGF), inflammatory cytokine(s), and the like, wherein inhibitor(s) of cytochrome P-450 are combined with said "pentoxifylline or functional derivatives/metabolites thereof."

MCM samples obtained from patients with liver disease have been found to stimulate fibroproliferation and collagen synthesis. The ability of these MCM samples to stimulate proliferation of fibroblasts is reduced (though not totally blocked) by preincubation of MCM with PDGF antibody. These results indicate that MCM obtained from patients with liver disease upregulates c-fos and c-jun gene expression in dermal fibroblasts. MCM samples from such patients significantly stimulate c-fos and c-jun mRNA compared to basal levels. These results indicate that the stimulation of fibroproliferation which occurs with MCM samples from patients with liver disease likely involves an upregulation in c-fos and c-jun gene expression. The results also indicate that the stimulation of c-fos and c-jun mRNA by MCM samples from such patients is not altered by 30 minute incubation with pentoxifylline. These results indicate that the effect of pentoxifylline on fibroproliferation stimulated by MCM samples from a liver disease patients is likely not due to an effect on c-fos or c-june gene expression.

The fibroproliferation stimulated by the liver disease patient's MCM was partially attenuated by PDGF antibody, indicating that PDGF is one of the components of the MCM involved in the stimulation of proliferation. It has previously been established that PDGF stimulates proliferation of skin fibroblasts (see Peterson, T. C. in Hepatol. 17(3):486–493 (1993) and Peterson et al., in Immunopharmacol. 28:259–270 (1994)) and myofibroblasts (see Isbrucker and Peterson in Hepatol. 22:4 (1995)). Pentoxifylline has been shown to block PDGF-stimulated fibroproliferation in a dose related manner (see Peterson et al., in Immunopharmacol. 28:259–270 (1994)). Pentoxifylline inhibits proliferation with a similar $IC_{50}$ to trapidil (see Peterson et al., supra), a drug reported to act at the PDGF receptor (see Kuratsu and Ushio in Neurosurg. 73:436–40 (1990) but pentoxifylline does not compete for the PDGF receptor (see Slysz and Peterson, supra). An interference in the post-receptor signalling of PDGF by pentoxifylline is a reasonable mechanism to investigate because pentoxifylline can increase intracellular cAMP (see Meskini et al., in Biochem. Pharmacol. 47:781–788 (1994) and Bessler et al., in J. Leukocyte Biol. 40:747–754 (1986)) and compounds that elevate cAMP have been reported to inhibit PDGF postreceptor signalling (see Wu et al., in Science 262:1065–9 (1993)).

It has previously been reported that the MCM obtained from patients with liver disease contains IL-1 and activated oxygen intermediates (see Peterson in Biochem. Pharmacol. 43(5):1166 (1992)) in addition to PDGF. It is likely that these and other factors contribute to the proliferative effect of MCM because PDGF antibody only partially reduces the fibroproliferative activity of the MCM. A recent report (see Lo et al., in J. Biol. Chem. 271:15703–7 (1996)) suggests that these other factors can stimulate immediate early gene expression, thus suggesting that the increased expression of these genes induced by MCM likely represents the combined effect of several factors. The lack of effect of pentoxifylline on MCM induced c-jun is likely due to the complex nature of the MCM and the variable effect of pentoxifylline on the individual components of the MCM. Since it has previously been established that the effect of PDGF on proliferation is blocked by pentoxifylline, the effect of PDGF on immediate early gene expression, and its potential modification by pentoxifylline was investigated.

The results of these investigations indicate that PDGF stimulates c-fos expression and that the induction is not reduced by pentoxifylline. These results are in agreement with several reports suggesting that PDGF will stimulate c-fos gene expression (see, for example, Marra et al., in FEBS Lett. 376:141–5 (1995), Buchdunger et al., in Cancer Res. 56:100–4 (1996), Rosenwald et al., in Cell Prolif. 28:631–44 (1996) and Terano et al., in Lipids S301–4 (1996)). Thus, the stimulation of c-fos mRNA by PDGF is maintained when cells are exposed to pentoxifylline. In contrast, however, PDGF stimulated fibroproliferation is abolished when the cells are exposed to pentoxifylline. These results indicate that the action of pentoxifylline on PDGF stimulated fibroproliferative activity is not via an effect on PDGF receptor signalling, through c-fos, or through c-fos itself.

PDGF postreceptor signalling was then studied to understand the action of PDGF on proliferation of fibroblasts. Though the fact that PDGF upregulates c-fos expression was known and assumed to play a major role in the mitogenic effects of PDGF, the upregulation of c-jun expression by PDGF and its potential role in proliferation has not been previously described. The results obtained herein indicate that PDGF increases c-jun expression 7-fold over basal expression.

The PDGF receptor is a tyrosine kinase receptor which upon activation transmits signals to mitogen activated protein kinases (MAP kinases). MAP kinases are a family of extracellular signal regulated kinases whose enzyme activity is increased in response to most mitogens, such as those acting on the receptor protein tyrosine kinases (see, for example, Krespo et al., in J. Biol. Chem. 269:21103–21109 (1994) and Palech, S. L., in Curr. Biol. 3:513–516 (1993)). This signalling from the PDGF receptor includes a cascade of protein kinases. The MAP kinases are phosphorylated, thereby increasing their enzymatic activity (see McCormick, F. in Nature 363:15–16 (1993) and Schlesinger, J. in Trends Biochem. Sci. 18:273–275 (1993)). In turn the MAP kinases phosphorylate and regulate the activity of key enzymes and nuclear proteins (Davis, R. J. J. Biol. Chem. 268:14553–14556 (1993)) which are responsible for increased expression of the c-fos gene.

Jun kinase controls the activity of c-jun, which then complexes with c-fos to make the AP-1 transcription factor. Homodimers of the jun protein product or heterodimeric complexes of jun-fos form the AP-1 nuclear transcription factor which controls the expression of genes possessing this regulatory element, including genes involved in proliferation (see, for example, Schafer et al., in Biochem. Biophys. Res. Commun. 221:111–6 (1996) and Bamberger et al., in Proc. Natl. Acad. Sci. USA 93:6169–74 (1996)).

The role of these two nuclear proteins was assessed because the activity of AP-1 is regulated at the level of jun and fos gene transcription (see Herschman, H. in Ann. Rev. of Biochem. 60:281–319 (1991) and Hunter and Karin in Cell 70:375–387 (1992)). The results obtained indicate that both c-fos and c-jun are upregulated by PDGF.

It is well accepted that PDGF activates MAP kinase (see Coso et al., in J. Biol. Chem. 270:5620–5624 (1995)). However, consistent with the results obtained herein, a recent paper suggests that PDGF may also activate Jun kinase (see Bogoyevitch, et al., in J. Biol. Chem. 270(50) :29710–17 (1995)). The mechanism for this effect is not known, but PDGF may activate both pathways via an effect on Ras. Recent results suggest that Ras activation results in phosphorylation of Jun kinase and MAP kinase (see Xie and Hershcan in J. Biol. Chem. 270:27622–28 (1995)). The results reported herein clearly show that PDGF rapidly and reproducibly increases the gene expression of both c-fos and c-jun.

To study the mechanism of action of pentoxifylline in the inhibition of PDGF-stimulated proliferation, the effect of pentoxifylline on PDGF postreceptor signalling was determined. Ultimately an inhibitory effect on the pathway that leads from PDGF to c-fos or from PDGF to c-jun (or both) would block proliferation. The results presented herein indicate that PDGF upregulates both c-fos and c-jun expression in dermal fibroblasts and that pentoxifylline preferentially inhibits the upregulation of c-jun. A recent report suggests that compounds that elevate cAMP may act upstream from MAP kinase at the Ras-Raf interaction (see Burgering et al., in EMBO Journal 12:4211–29 (1993)). Such an interaction would be expected to alter c-fos expression. In contrast, the results presented herein would suggest that pentoxifylline does not affect the Ras-Raf interaction, but instead interferes with an alternate PDGF signalling pathway which signals from Ras through Jun kinase, or a pathway which crosstalks between MAP kinase and Jun kinase. Accordingly, pentoxifylline would only alter the expression of c-jun and not affect the expression of c-fos.

The results presented herein provide evidence for the induction of c-jun expression by PDGF and provides a mechanism for the inhibitory effect of pentoxifylline on PDGF stimulated proliferation by altering PDGF post-receptor signalling. An understanding of this mechanism of action could prove to be of great importance, since an elevation in PDGF has been implicated in a wide variety of diseases and/or conditions, including interstitial lung diseases (see, for example, Uebelhoer et al., in Chest. 107:701–5 (1995) and Shaw et al., in Am. Rev. Respir. Dis. 143:167–73 (1991)), glomerular nephritis (see, for example, Gesualdo et al., in Lab Invest. 65:160–7 (1991)), nephritis associated with systemic lupus (see, for example, Nakamura et al., in Clin. Immunol. Immunopathol. 63:173–81 (1992)), liver fibrosis (see, for example, Peterson and Isbrucker in Hepatol. 15(2):191–197 (1992)), Graves' ophthalmopathy (see, for example, Imai et al., in Acta Endocrinol. Copenh. 126:541–52 (1992)), drug induced ergotism (see, for example, Pietrogrande et al., in Angiology 46:633–6 (1995)), cardiovascular disease (see, for example, Ciminiello et al., in Angiology 45:289–93 (1994) and Pesonen, E. in Eur. Heart J. 15 Suppl C:57–61 (1994)), cancer (see, for example, Ross et al., in Cancer Epidemiol. Biomarkers Prev. 4:485–9 (1995)), and the like.

In accordance with another embodiment of the present invention, there are provided in vitro assays to determine whether pentoxifylline or functional derivatives/metabolites thereof are likely to be effective for treatment of a subject afflicted with a disease and/or condition characterized by one or more of the following:

elevated PDGF levels, elevation of Jun kinase, elevation of c-jun, activation of NF-kappaB or NF-kappaB p65, neutrophil infiltration, or elevated levels of inflammatory cytokine(s), said method comprising determining the uptake by test cells in suitable media therefor, of a labeled building block indicative of cell proliferation, wherein said uptake is determined in the presence of serum obtained from said subject, and in the presence and absence of pentoxifylline or functional derivatives/metabolites thereof, wherein test cells suitable for use herein are selected from the group consisting of fibroblasts, glial cells, smooth muscle cells and transformed cells obtained from the particular organ of interest, and wherein reduction of uptake by test cells of labeled building block in the presence of pentoxifylline or functional derivatives/metabolites thereof, relative to the uptake by test cells of labeled building block in the absence of pentoxifylline or functional derivatives/metabolites thereof, is predictive of the efficacy of pentoxifylline or functional derivatives/metabolites thereof for the treatment of diseases or conditions characterized as set forth above.

As employed herein, the phrase "labeled building block" refers to any compound which is taken up by DNA during active DNA synthesis, wherein such compound can be readily detected by any suitable means. Such labeled materials can be rendered detectable by a variety of means, e.g., as a result of radioactive labeling, by calorimetric detection, and the like. Examples of suitable labeled building blocks contemplated for use herein include tritiated thymidine, bromouridine, and the like.

Suitable test cells contemplated for use herein include fibroblasts, glial cells, smooth muscle cells or transformed cells derived from the organ which is the disease target, e.g., liver myofibroblasts are useful to test sera samples from liver fibrosis patients, pulmonary fibroblasts or smooth muscle cells (mesenchymal cells) are useful to test sera samples from pulmonary fibrosis patients, glial cells are useful to test sera samples from Alzheimer's patients, intestinal fibroblasts and intestinal smooth muscle cells are useful to test sera samples from patients with inflammatory bowel disease, and the like. Other test cells contemplated for use herein include cultured human skin fibroblasts, vascular smooth muscle cells, mesangial cells (kidney), hematopoietic cells (leukemias), Kaposi sarcoma-derived cells (Kaposi sarcoma), epithelial cells, and the like.

As readily recognized by those of skill in the art, suitable media appropriate for use with a test cell will depend on the particular test cell being employed. Those of skill in the art can readily determine appropriate media to employ once the test cell of choice has been identified.

In accordance with yet another embodiment of the present invention, there are provided kits which are useful for assays to determine whether pentoxifylline or functional derivatives/metabolites thereof are likely to be effective for treatment of diseases and/or conditions characterized by one or more of the following:

elevated PDGF levels, elevation of Jun kinase, elevation of c-jun, activation of NF-kappaB or NF-kappaB p65, neutrophil infiltration, or elevated levels of inflammatory cytokine(s), said kit comprising:

cultured cells selected from the group consisting of fibroblasts, glial cells, smooth muscle cells and transformed cells obtained from the particular organ of interest, in suitable media therefor, pentoxifylline or functional derivatives/metabolites thereof, and labeled building block indicative of cell proliferation.

Cultured cells contemplated for use herein include human skin fibroblasts, intestinal smooth muscle cells, liver myofibroblasts, pulmonary fibroblasts, mesenchymal cells, glial cells, intestinal fibroblasts, intestinal smooth muscle cells, vascular smooth muscle cells, mesangial cells, hematopoietic cells, Kaposi sarcoma-derived cells, epithelial cells, and the like.

In accordance with a still further embodiment of the present invention, there are provided methods to quantify the collagen content of a tissue sample, said method comprising:

rolling said tissue sample longitudinally, fixing said sample in formalin, and embedding said sample in paraffin, sectioning said sample, deparaffinizing a section of said sample and staining said sample with Sirius red and Fast green, removing said dyes from the stained sections, and determining the collagen concentration of said sample.

Thus, collagen concentrations in a variety of tissues (e.g., colonic tissue, heart tissue, brain tissue, lung tissue, and the like) can be determined by removing the desired tissue for analysis from the host and treating the tissue as described herein. The specific dyes employed allow one to distinguish collagenous protein from non-collagenous protein since Sirius red stains collagenous protein while Fast green stains non-collagenous protein. These dyes can be removed from the tissue sections using suitable solvent, e.g., sodium hydroxide methanol solution, and the collagen concentration determined with reference to the maximal absorbance of Sirius red and Fast green.

The invention will now be described in greater detail by reference to the following non-limiting examples.

EXAMPLE 1

Details of Blood Test

Fibroproliferative activity of sera (500 µl) and/or monocyte conditioned medium (MCM) samples (500 µl) is assessed by tritiated thymidine uptake using cultured human skin fibroblasts and/or intestinal smooth muscle cells (ATCC). Pentoxifylline (Sigma Chemical Company, St. Louis, Mo.) is tested at 240 µM. MCM is prepared from peripheral blood (10 ml) as has previously been described (see Peterson in Hepatol. 15(2):191–197 (1992)).

To assess fibroproliferative activity, medium is removed by aspiration from flasks containing confluent intestinal smooth muscle cells or monolayers of human fibroblasts (at passage 5 to 12). The cells are briefly rinsed with 10–20 ml of sterile saline to remove any remaining medium. Fibroblasts are removed from the flasks by the addition of 5 ml trypsin-EDTA (Gibco, Ontario, Canada) for 30 seconds with gentle rocking at room temperature, followed by pouring off of most of the trypsin solution and incubation at 37° C. for 3–5 minutes.

Cells are resuspended in 10 ml Dulbecco's (DBE, Gibco, Canada), antibiotic/antimycotic (Gibco, Canada) and 0.5% CPSR-2 (Sigma Chemical Co., St. Louis, Mo.). CPSR-2 is a serum replacement (control processed serum replacement-2) which has low mitogenic activity. Two hundred microliter aliquots of cell suspension ($8\times10^3$ cells) are added to 0.32 cm² flat bottom wells of 96 well microtiter plates and incubated for 24 hours at 37° C. in 5% $CO_2$ in air. The media are removed from each well by aspiration, replaced by 200 µl of DBE supplemented with factors incubated as above for a further 22 hours.

PDGF A/B, (R&D Systems Inc. Minneapolis, Minn.) 8 ng/ml is the positive control and is used to stimulate proliferation of fibroblasts in the presence or absence of pentoxifylline (Sigma Chemical Co., St. Louis, Mo.).

Methyl-$^3$H-thymidine 0.5 µCi (Amersham, Ontario, Canada) is added to each well and the incubation continued for an additional 2 hours. To harvest the fibroblasts, the medium is removed by aspiration and replaced by 100 µl of trypsin-EDTA for a few minutes at 37° C. This trypsinization is verified as sufficient to detach all fibroblasts. The loose fibroblasts are then aspirated onto glass fiber filters using a Brandel Cell Harvester (Xymotech Biosystems, Ontario, Canada), washed 8–10 times with phosphate buffered saline and the radioactivity is determined by liquid scintillation. All samples are tested in quadruplicate. The $^3$H-thymidine uptake assay has been verified as a good measure of proliferation of fibroblasts, in response to stimuli or inhibitors, by manual cell counts and MTT assay.

The results produce a patient disease index (PDI) and a drug sensitivity index (DSI).

EXAMPLE 2

Fibroproliferation

The fibroproliferative activity of PDGF was assessed by modification of the triated thymidine incorporation method of Dohlman et al. in Immunol. 52:577–584 (1984) using normal human skin fibroblasts as reported by Peterson (see Hepatol. 15(2):191–197 (1992)). Briefly, cells were resuspended in Dulbecco's (DBE, Gibco, Canada), antibiotic/antimycotic (Aa, Gibco, Canada) and 0.5% CPSR-2 (Sigma Chemical Co., St. Loius, Mo.). CPSR-2 is a serum replacement (control processed serum replacement-2) which has low mitogenic activity. Two hundred microliter aliquots of cell suspension ($8\times10^3$ cells) are added to 0.32 cm² flat bottom wells of 96 well microtiter plates and incubated for 24 hours at 37° C. in 5% $CO_2$ in air. The media are replaced by 200 µl of DBE supplemented with factors incubated as above for a further 22 hours. PDGF B/B, (R&D Systems Inc. CA) 8 ng/ml is used to stimulate proliferation of fibroblasts in the presence or absence of pentoxifylline (Sigma Chemical Co., St. Louis, Mo.).

Monocyte conditioned medium (MCM) is prepared from monocytes obtained from patients with liver disease, as previously described by Peterson in Hepatol. 15(2):191–197 (1992)). Samples are assessed for their ability to stimulate fibroproliferation and also assessed for the effect of pentoxifylline on that proliferative effect. Methyl-$^3$H-thymidine 0.5 µCi (Amersham Canada) is added to each well, incubated for an additional 2 hours and then the cells are harvested by aspiration onto glass fiver filters using a Brandel Cell Harvester (Xymotech Biosystems, Ontario, Canada) and the radioactivity is determined by liquid scintillation. All samples are tested in quadruplicate. The $^3$H-thymidine uptake assay has been validated by manual cell counts and MTT assay as a measure of fibroblast number following treatment with either proliferative or antiproliferative agents (see, for example, Peterson et al., in Immunopharmacol. 28:259–270 (1994) and Denizat & Lang, in Immunol. Methods 89:271–277 (1986)).

EXAMPLE 3

Assessment of Immediate Early Gene Expression

The effect of MCM obtained from patients with liver disease on c-fos and c-jun expression and the effect of pentoxifylline on this gene expression is assessed. To do this, MCM is prepared from blood samples obtained from 6 patients with liver disease as previously described (see Peterson and Isbrucker in Hepatol. 15(2):191–197 (1992)). Fibroblasts are then incubated with MCM for 30 min with and without addition of pentoxifylline prior to assessment of c-fos and c-jun mRNA.

Measurement of c-fos and c-jun mRNA is done by Northern analysis using specific oligomers. mRNA was isolated from dermal fibroblasts using Ribosept kits (VWR, Canada). RNA is subjected to electrophoresis overnight in a denaturing 1% agarose gel, transferred onto a Nytrans⁺ nylon membrane (ICN Biomedicals Inc., Montreal, Canada) and cross-linked with an ultraviolet crosslinker (Stratagene UV Stratalinker 2400). Specific probes (45-mer) for human c-fos and human c-jun as follows are obtained from Genosys.

Probes are labelled with $^{32}$P using 3'-endlabelling kit (Amersham, Canada). Blots are subsequently stripped and reprobed with $^{32}$P-labelled β-actin as internal control. Initial experiments allow one to optimize conditions and show that c-fos mRNA is increased in dermal fibroblasts treated with PDGF for 30 min compared to controls.

The effect of pentoxifylline on PDGF stimulated c-fos and c-jun gene expression is also assessed by Northern analysis using mRNA prepared from dermal fibroblasts which had been treated with PDGF (8 ng/ml) for 30 min (in the presence and absence of pentoxifylline) for 30 min and 2 hrs.

Statistical analysis. An unpaired Students t test is used to compare two variables, and an analysis of variance (ANOVA) and Student-Neuman-Keuls test is used when more than 2 variables were compared (see Zar, J. H. in Biostatistical methods. Prentice-Hall (Englewood Cliffs, N.J., 1974)).

Results. Monocyte conditioned medium (MCM) samples obtained from six patients with liver disease are seen to stimulate proliferation of fibroblasts 2.5-fold over basal proliferation (see FIG. 1A). Incubation of MCM samples with pentoxifylline significantly reduced the effect of MCM on proliferation in an concentration related manner (see FIG. 1B). Preincubation of MCM with PDGF antibody (50 μg/ml) significantly reduced the fibroproliferative effect. This indicates that one of the components of the MCM which stimulates proliferation is PDGF (see FIG. 1C).

The hypothesis that the stimulation of fibroproliferation which occurs with MCM samples from a liver disease patient involves an upregulation in c-fos gene expression due to the presence of PDGF was then tested. A Northern blot of such samples shows the effect of MCM obtained from a liver disease patient on c-fos and c-jun gene expression in human fibroblasts and clearly indicates that MCM obtained from patients with liver disease increases the production of c-fos and c-jun mRNA in fibroblasts. Phosphorimaging analysis showed that MCM increased c-fos and c-jun mRNA 6-fold and 2-fold, respectively.

To test the hypothesis that the upregulation in c-fos and c-jun gene expression by MCM samples obtained from a liver disease patient is downregulated by pentoxifylline, mRNA was also assessed from cells treated with MCM in the presence of pentoxifylline. The results indicate that the upregulation in c-fos and c-jun which occurs due to exposure of fibroblasts to MCM obtained from patients with liver disease is not inhibited by 30 min of exposure of MCM to pentoxifylline. The results also show that pentoxifylline did not alter c-fos and c-jun mRNA levels. It is of interest to note that this same concentration of pentoxifylline was sufficient to abolish MCM stimulated fibroproliferation by 95% (see FIG. 1B).

MCM contains PDGF but also contains other factors including IL-1 and activated oxygen intermediates which can stimulate proliferation and could potentially stimulate c-fos and/or c-jun and which individually may or may not be inhibited by pentoxifylline. On the other hand it has been established that PDGF stimulates proliferation and that this effect is blocked by pentoxifylline. Further study, therefore, focussed on PDGF itself. Thus, tests were conducted to determine whether the effect of PDGF on proliferation involves upregulation of immediate early genes and whether the actions of pentoxifylline are the result of changes in immediate early gene expression.

C-fos and c-jun gene expression in skin fibroblasts stimulated to proliferate with PDGF in the presence and absence of pentoxifylline was then assessed, compared to controls (cells stimulated with basal medium alone). Thus, the effect of PDGF, with and without pentoxifylline, on the expression of c-fos and c-jun can be visualized by Northern blot, wherein the following are compared:

mRNA isolated from fibroblasts incubated in basal medium;

mRNA isolated from fibroblast samples stimulted with PDGF (8 ng/ml);

mRNA from skin fibroblasts stimulated with PDGF plus pentoxifylline (3.5 mM);

mRNA levels in skin fibroblasts stimulated with pentoxifylline alone.

The blots are probed with the 45-mer for c-fos described above (SEQ ID NO:1), the 45-mer for c-jun described above (SEQ ID NO:2), and oligomer for β-actin.

Thus, incubation of PDGF (30 min) increases c-fos and c-jun expression in skin fibroblasts. Phosphorimaging analysis shows that PDGF causes increased levels of c-fos and c-jun mRNA 2-fold and 7-fold, respectively. Pentoxifylline itself did not alter c-fos or c-jun mRNA levels in control cells and did not reduce the level of c-fos mRNA in cells treated with PDGF. However, pentoxifylline markedly reduced c-jun mRNA levels in cells treated with PDGF. Phosphorimaging analysis also shows that pentoxifylline decreases c-jun mRNA (53%) in cells treated with PDGF compared to cells treated with PDGF alone.

When the same blot is probed with a β-actin probe, equal loading in all four lanes of the blot is verified. Phosphorimaging analysis of results obtained from 3 independent experiments indicates that PDGF significantly increases the expression of c-jun and c-fos, and that pentoxifylline significantly reduces the expression of c-jun, but does not alter c-fos expression induced by PDGF.

Cells treated in the same manner were also assessed for fibroproliferative activity. The results (see FIG. 2) verify that this concentration of PDGF (8 ng/ml) stimulates proliferation and that this concentration of pentoxifylline (3.5 mM) blocks proliferation of fibroblasts.

EXAMPLE 4

Collagen Assay

Collagen concentration in colonic tissue is determined using the method of Lopez de Leon and Rojkind (see J. Histochem. and Cytochem. 33(8):737–743 (1985)). Colons are dissected from rats and rolled longitudinally, fixed in formalin and embedded in paraffin for sectioning. Sections of colon (8 mm) are deparaffinized and stained with Sirius red and Fast green. Sirius red stains collagenous protein while Fast green stains non-collagenous protein. The dyes are then removed from these sections using sodium hydroxide methanol solution and the collagen concentration determined with reference to the maximal absorbance of Sirius red and Fast green.

While the invention has been described in detail with reference to certain preferred embodiments thereof, it will be understood that modifications and variations are within the spirit and scope of that which is described and claimed.

That which is claimed is:

1. A method for the treatment of a human subject afflicted with a disease or condition characterized by one or more of the following:

elevated platelet derived growth factor (PDGF) levels, elevation of Jun kinase, elevation of c-jun, or activation of NF-kappaB or NF-kappaB p65, provided that said disease or condition is not collagenous colitis, said method comprising administering to said subject an amount of pentoxifylline or functional derivatives metabolites thereof effective to ameliorate the symptoms of said disease.

2. The method according to claim 1 wherein said disease or condition is interstitial lung disease, human fibrotic lung disease, human kidney disease, glomerular nephritis, nephritis associated with systemic lupus, liver fibrosis, myocardial fibrosis, pulmonary fibrosis, Grave's ophthalmopathy, drug induced ergotism, cardiovascular disease, cancer, Alzheimer's disease, scarring, scleroderma, glioblastoma in Li-Fraumeni syndrome, sporadic glioblastoma, myeloid leukemia, acute myelogenous leukemia, myelodysplastic syndrome, myeloproliferative syndrome, gynecological cancer, Kaposi's sarcoma, Hansen's disease or inflammatory bowel disease not including collagenous colitis.

3. The method according to claim 1 wherein said pentoxifylline or functional derivatives/metabolites thereof are delivered orally, transdermally, intravenously, intramuscularly, topically, by inhalation or rectally.

4. The method according to claim 1 wherein said pentoxifylline or functional derivatives/metabolites thereof are delivered orally.

5. The method according to claim 1 wherein an effective amount of pentoxifylline or functional derivatives/metabolites thereof comprises in the range of about 200 mg–1 g per dose, administered to the subject at least two times a day.

6. The method according to claim 5 wherein said pentoxifylline or functional derivatives/metabolites thereof are administered to said subject at least four times a day.

7. The method according to claim 1 wherein said pentoxifylline or functional derivatives/metabolites thereof is administered to the subject by sustained release.

8. The method according to claim 1 wherein said pentoxifylline or functional derivatives/metabolites thereof are selected from the group consisting of 1-(5-oxohexyl)-3,7-dimethylxanthine (pentoxifylline), 1-(5-hydroxyhexyl)-3,7-dimethylxanthine (metabolite-1), and propentofylline.

9. The method according to claim 1 wherein said pentoxifylline or functional derivatives/metabolites thereof are administered in combination with an inhibitor of cytochrome P-450.

10. The method according to claim 1 further comprising monitoring the level of pentoxifylline or functional derivatives/metabolites thereof in serum from said patient, and adjusting the dosage of pentoxifylline or functional derivatives/metabolites thereof based on the level detected in the patient's serum.

11. An in vitro assay to determine whether pentoxifylline or functional derivatives/metabolites thereof are effective for treatment of a human subject afflicted with a disease and/or condition characterized by one or more of the following:

elevated PDGF levels, elevation of Jun kinase, elevation of c-jun, activation of NF-kappaB or NF-kappaB p65, neutrophil infiltration, or elevated levels of inflammatory cytokine(s), said method comprising determining the uptake by test cells in suitable media therefor, of a labeled building block indicative of cell proliferation, wherein said uptake is determined in the presence of serum obtained from said subject, and in the presence and absence of pentoxifylline or functional derivatives/metabolites thereof, wherein test cells are selected from the group consisting of fibroblasts, glial cells, smooth muscle cells and transformed cells obtained from the particular human organ of interest, wherein said organ is derived from a human subject afflicted with said disease and/or condition, and wherein reduction of uptake by test cells of labeled building block in the presence of pentoxifylline or functional derivatives/metabolites thereof, relative to the uptake by test cells of labeled building block in the absence of pentoxifylline or functional derivatives/metabolites thereof, is predictive of the efficacy of pentoxifylline or functional derivatives/metabolites thereof for the treatment of diseases or conditions set forth above.

12. The assay according to claim 11 wherein said labelled building block is tritiated thymidine.

13. The assay according to claim 11 wherein said test cell is selected from liver myofibroblasts, pulmonary fibroblasts, smooth muscle cells, mesenchymal cells, glial cells, intestinal fibroblasts, intestinal smooth muscle cells, cultured human skin fibroblasts, vascular smooth muscle cells, mesangial cells, hematopoietic cells, Kaposi sarcoma-derived cells or epithelial cells.

14. The assay according to claim 11 wherein said test cells comprise a monolayer of cultured human skin fibroblasts.

15. The assay according to claim 11 wherein said test cells comprise confluent intestinal smooth muscle cells.

16. A kit to determine whether pentoxifylline or functional derivatives/metabolites thereof are likely to be effective for treatment of diseases and/or conditions characterized by one or more of the following:

elevated PDGF levels, elevation of Jun kinase, elevation of c-jun, activation of NF-kappaB or NF-kappaB p65, neutrophil infiltration, or elevated levels of inflammatory cytokine(s), said kit comprising:

cultured cells selected from fibroblasts, glial cells, smooth muscle cells and transformed cells obtained from the particular human organ of interest in suitable assay medium, wherein said organ is derived from a human subject afflicted with said disease and/or condition, pentoxifylline or functional derivatives/metabolites thereof, and labeled building block indicative of cell proliferation.

17. The kit according to claim 16 wherein said cultured cells are selected from human skin fibroblasts, intestinal smooth muscle cells, liver myofibroblasts, pulmonary fibroblasts, mesenchymal cells, glial cells, intestinal fibroblasts, intestinal smooth muscle cells, vascular smooth muscle cells, mesangial cells, hematopoietic cells, Kaposi sarcoma-derived cells or epithelial cells.

18. The kit according to claim 16 wherein said labeled building block is tritiated thymidine or bromouridine.

19. The kit according to claim 16 further comprising PDGF-AA, PDGF-BB, PDGF-AB, TNF, IL-1, IL-4, IL-12, IGF-1, IGF-2, TGF-alpha, TGF-beta, EGF, NGF, aFGF or bFGF.

20. A method to quantify the collagen content of a human tissue sample, said method comprising:

rolling said human tissue sample longitudinally, fixing said sample in formalin, and embedding said sample in paraffin, sectioning said sample, deparaffinizing a section of said sample and staining said sample with Sirius red and Fast green, removing said dyes from the stained sections, and determining the collagen concentration with reference to the maximal absorbance of Sirius red and Fast green.

* * * * *